United States Patent

Bauer et al.

[11] Patent Number: 5,934,470
[45] Date of Patent: Aug. 10, 1999

[54] METHOD AND PACKAGE FOR COMPRESSED DIAPERS

[75] Inventors: Rainer Richard Bauer, Wiesbaden; Klaus Karl Ferdinand Haubach, Ludwigshafen, both of Germany

[73] Assignee: The Procter & Gamble Company, Cincinnati, Ohio

[21] Appl. No.: 08/872,570

[22] Filed: Jun. 10, 1997

Related U.S. Application Data

[63] Continuation of application No. 08/532,732, filed as application No. PCT/US94/02812, Mar. 16, 1994, abandoned.

[30] Foreign Application Priority Data

Mar. 30, 1993 [EP] European Pat. Off. .............. 93870057

[51] Int. Cl.⁶ .................................................. B65D 71/06
[52] U.S. Cl. ........................................... 206/494; 206/497
[58] Field of Search ................................... 206/432, 449, 206/494, 497; 53/436, 438, 528, 529, 399

[56] References Cited

U.S. PATENT DOCUMENTS

| | | |
|---|---|---|
| 2,979,871 | 4/1961 | Kieckhefer . |
| 3,197,062 | 7/1965 | Day et al. .............................. 206/494 |
| 3,231,083 | 1/1966 | Rumsey, Jr. . |
| 3,327,449 | 6/1967 | Hullhorst et al. . |
| 3,407,562 | 10/1968 | Nicola . |
| 3,918,584 | 11/1975 | Richardson . |
| 4,506,801 | 3/1985 | Origuchi . |
| 4,799,350 | 1/1989 | Rias . |
| 4,821,491 | 4/1989 | Rias . |
| 5,022,216 | 6/1991 | Muckenfuhs et al. . |
| 5,027,582 | 7/1991 | Dearwester . |
| 5,036,978 | 8/1991 | Frank et al. ............................. 206/494 |
| 5,048,687 | 9/1991 | Suzuki et al. . |
| 5,050,742 | 9/1991 | Muckenfuhs . |
| 5,054,619 | 10/1991 | Muchenfuhs . |
| 5,163,558 | 11/1992 | Palumbo et al. . |
| 5,361,905 | 11/1994 | McQueeny et al. .................... 206/494 |
| 5,377,837 | 1/1995 | Roussel .................................. 206/494 |
| 5,392,912 | 2/1995 | Grubbs .................................. 206/497 |
| 5,443,161 | 8/1995 | Jonese .................................. 206/494 |

FOREIGN PATENT DOCUMENTS 0 413 122 A1  2/1991  European Pat. Off. .

*Primary Examiner*—Paul T. Sewell
*Assistant Examiner*—Luan K. Bui
*Attorney, Agent, or Firm*—Jack L. Oney, Jr.; William Scott Andes

[57] ABSTRACT

A package (10) for compressed flexible articles comprising one or more unit packages (20), wherein each unit package comprises more than one compressed flexible article (21), said unit packages being surrounded by a covering made from a film (15) of thermoplastic material characterised in that each unit package is maintained in its compressed condition by a paper wrapping (12).

4 Claims, 5 Drawing Sheets

METHOD AND PACKAGE FOR COMPRESSED DIAPERS

This is a continuation of application Ser. No. 08/532,732, filed as PCT/US94/02812 Mar. 16, 1994, now abandoned.

BACKGROUND OF THE INVENTION

This invention relates to packaging for compressed, flexible articles, especially disposable absorbent products such as diapers. In particular the invention aims to reduce the overall weight (and cost) of packing materials required for compressed, flexible articles, and, furthermore to replace some of the plastic packaging with paper packaging, which can be more readily recycled. Also, it is possible to use a greater proportion of recycled materials in the packaging than previously, without compromising the appearance of the package.

Flexible articles, such as disposable diapers, have been compressed prior to packing and shipping for about the last 5 years. It is intended that the total volume of the flexible articles should be greatly reduced prior to sale. This allows the consumer to reduce purchase frequency, as well as being more economical in use of space.

Although, it has been suggested to make the packaging material either partly or completely from paper the practice has been to use plastic materials. One of the disadvantages of this trend, however, has been the need to use higher strength packaging materials (eg. plastic sheets or foils) in order to maintain the flexible articles in their compressed state without tearing the package.

EPA 349 050, published on Jan. 3, 1990, relates to flexible bags filled with compressed flexible articles. This application focuses on an improved opening device which is able to resist the tearing force of the compressed flexible articles without the need for any reinforcing material. Although the application says that "the bag can be made of any flexible material, like different types of plastic film, paper, or any combination of those", it does not, however, teach the benefits of a paper inner container to resist expansion forces of the compressed articles, in combination with a light-weight plastic outer covering.

EPA 425 008, published on May 2, 1991, discloses a paper bag used to compactly pack compressed flexible articles. The application states that the polyethylene bags of the prior art, when filled with compressed flexible articles have certain disadvantages, in particular the poor biodegradability of polyethylene and the lack of suitable recycling facilities. This problem is solved by the use of paper as a more environmentally friendly outer container. However there is no suggestion that a paper inner container could be advantageously combined with a plastic outer covering.

Other patents have addressed the problems of methods of packaging flexible materials in order to maintain a high level of compression.

U.S. Pat. No. 3,327,449, published on Jun. 27th, 1967, relates to a method of compressing and packing insulating batts in a paper wrapping. The invention aims to provide a high level of compression to the batts, and to maintain it through the packing process. It does not disclose a paper wrapping in combination with a plastic outer covering.

U.S. Pat. No. 5,022,216, published on Jun. 11th, 1991, relates to a method and apparatus for filling a flexible bag with compressed articles. The bag may be comprised of "polymeric films, papers, nonwovens, or a laminate comprising two or more of such materials, thereby decreasing the severity of the disposal problem from an environmental standpoint both with respect to the amount of packaging material required and the disposability/degradability of the particular bag material selected", (Column 2, lines 50–56). It does not teach the combination of paper and plastic packaging materials.

It has now been recognised that the prior art still leaves problems of optimisation of a packaging system (optimisation from the point of view of both weight and cost of packaging per number of articles packed). Furthermore, the packaging systems of the prior art still leave the problem of cost effective package that can be both made from recycled materials, and which can be readily recycled again after use. It has been common practice to print designs or decoration on to plastic coverings despite the fact that this makes it difficult to recycle such plastic materials.

The present invention has identified that this problem can be addressed by decoupling the internal stresses upon the package (caused by the compression of the flexible articles) from the external "stresses" upon the packaging (caused by environmental influences such as water, humidity, dust etc.). The claimed invention proposes a solution of using a paper wrapping to resist the internal stresses in one or more sub-units, and a thin plastic film to resist these external "stresses".

It is also an aim of the invention to improve the ease of recycling of the packaging material. This is achieved by using a transparent plastic film and printed paper wrapper. This is an improvement over printed plastic films of the prior art because printed paper can be more easily de-inked prior to recycling than printed plastic films.

It is a further aim of the invention to provide a package which can be easily carried and opened by the consumer.

SUMMARY OF THE INVENTION

A package for compressed flexible articles comprising one or more unit packages, wherein each unit package comprises more than one compressed flexible article, said unit packages being surrounded by a covering made from a film of thermoplastic material wherein each unit package is maintained in its compressed condition by a paper wrapping which comprises at least four sides, at least two opposing sides of which are disposed parallel to the direction of compression of the compressed flexible articles.

In another aspect of the invention a method for making such a package is provided.

BRIEF DESCRIPTION OF THE DRAWINGS

The invention will be described hereinafter with reference to the following drawings:

FIG. 5 shows a schematic representation of alternative embodiments of a wrapping sleeve.

DETAILED DESCRIPTION OF THE INVENTION

Figure 1:
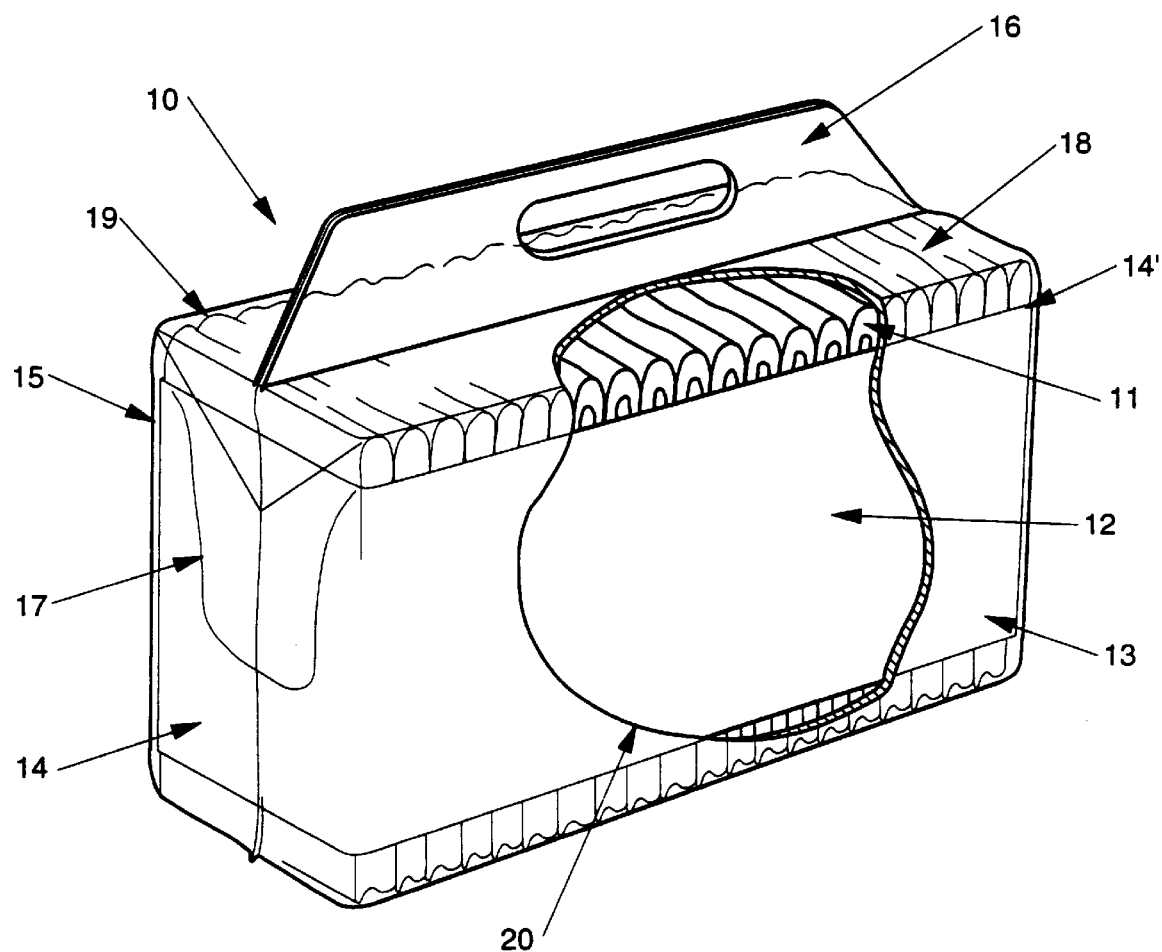
FIG. 1 shows a perspective view composite package which comprises a package retained within a wrapping sleeve.

The present invention is intended for use with any compressed flexible articles. Examples of such articles are disposable paper products such as diapers.

By the term "compression", it is meant that the flexible articles should be compressed in the package by at least 20% of their uncompressed thickness, and preferably by at least 30% of their uncompressed thickness. More preferably, the invention allows higher levels of compression, such as 40% or, even more preferably 60% of the uncompressed thickness. Levels of compression greater than 70% have been successfully achieved.

The present invention comprises three essential features: flexible articles; paper wrapping; and plastic covering, which are described in more detail below.

Flexible Articles

Although the present invention may be used with many types of flexible articles, it is particularly useful for disposable absorbent products such as diapers, incontinence products, sanitary napkins, absorbent pads and bandages. Such products are generally bulky in the uncompressed state. In many cases these products are of a composite nature, comprising an absorbent core and one or more flexible sheets. The core may itself be homogeneous or composite in structure. Such absorbent products often comprise a fluid permeable sheet (e.g. a non-woven or perforated polymeric film) which, in use, lies closest to the body of the wearer, and an outer barrier sheet.

Paper Wrapping

It is an essential feature of the present invention that the flexible articles are packed into one or more unit packages, and that each unit package is maintained in the compressed form by a wrapping. The essential features of the wrapping used in the present invention are that it should not tear under the force exerted by the compressed flexible articles contained within it; and it should not stretch to the extent that a substantial amount of the compressive forces would be transferred to the plastic covering.

A material which is formed as a cellulosic web, and which fulfils these requirements is suitable for use as the wrapping in the present invention. For example the cellulosic web may be a laminate, a bonded compressed air laid web, or a wet laid web, although wet laid paper wrapping is preferred due to its tensile properties. It is preferred that the inner wrapping should have a minimum tensile strength (measured in the machine direction, MD) of 4 kN/m, and a extensibility in the machine direction (at rupture) of not more than 1.04 times its original length. More preferably the paper wrapping should have a tensile strength in the machine direction of at least 6 kN/m, and a extensibility in the machine direction of not more than 1.025 times its original length.

Paper suitable for use in the present invention may have any basis weight provided that it fulfils the physical requirements defined above. However, it has been found that paper having a basis weight of at least 40 grams per square meter, and preferably about 70 grams per square meter is suitable.

In order to achieve the benefits of the lightweight package of the invention, the paper should most preferably have a basis weight of less than 125 grams per square meter.

The most preferred material of construction of the wrapping is a wet-laid paper made from wood- or manila fibres, or a mixture of these. Both virgin and recycled paper may be used.

Figure 5A:
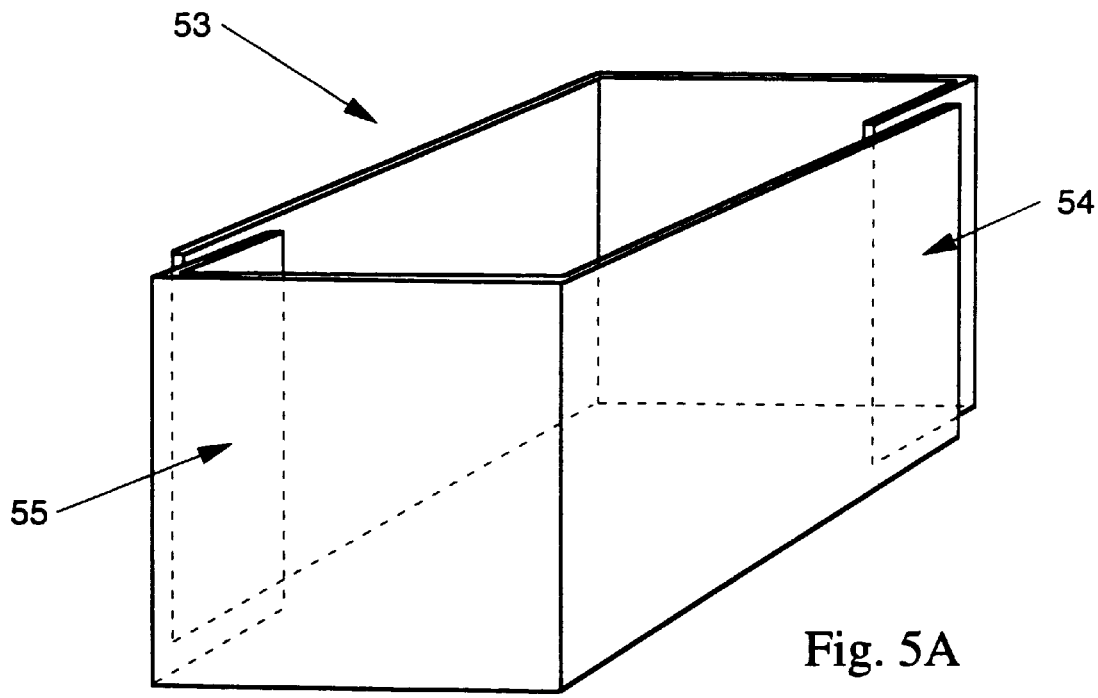
FIG. 5a shows a wrapping sleeve which comprises two paper sheets which are fixed or bonded together at two overlapping portions.
Figure 5B:
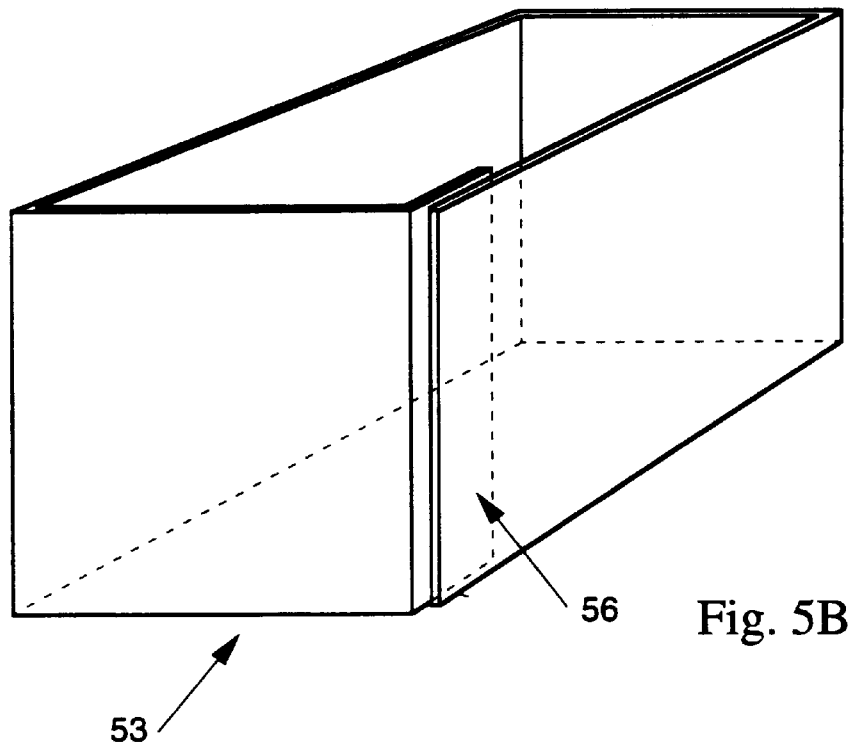
FIG. 5b shows a wrapping sleeve comprising one paper sheet which is fixed or bonded to itself at one overlapping portion.

The wrapping may be either folded and secured around the compressed flexible articles, or, alternatively it may be completely or partially preformed before the compressed flexible articles are retained within it. A wrapping may be preformed by folding a piece of wrapping material to take the external form of the unit package, and then securing the material to itself at an area of overlap (as shown in FIG. 5b). Alternatively, two or more pieces of the wrapping material may be folded and bonded to each other to form a suitable wrapping for the unit package (as shown in FIG. 5a).

The material encircling the compressed articles must be secured to itself at one or more areas of overlap in order to form the unit package, and in order to prevent the compressed flexible articles from returning to their expanded form. In order to do this, a means of securing two ends of the material together must be provided. This can be any of a variety of means such as stapling, welding, adhesion, bonding, gluing or a mechanical type of fastening (of the "Velcro" type). Many methods of securing a paper material to itself are known to the man skilled in the art. Some examples are hot melt glue, pressure sensitive glue or white (cold) glue, any of which may be applied by known techniques such as spraying, bars, spiral glue nozzles or slot extrusion nozzles. The glued surface may cover an area essentially corresponding to the whole of the area of overlap, or the glue may be laid to cover only a part of the area of overlap, for example in spots, lines or spirals.

In one embodiment of the invention the paper may be coated or laminated with heat-sealable polymeric materials such as polyethylene. This makes it possible to bond the paper to itself by applying heat to an area of overlap in order to complete the sleeve or wrapping.

It is an essential feature of the invention that at least two opposing sides of the wrapping are parallel with the direction of compression of the flexible articles, these opposing sides resist the force due to the compressed articles held within the sleeve. Best use of the physical properties of the wrapping material is achieved if the machine direction of the paper lies parallel with the direction of compression of the flexible articles.

In one particularly preferred embodiment of the invention, the paper sleeve takes the form of a four-sided sleeve which retains the flexible articles of the unit package in the compressed state.

It is anticipated that the paper wrapper will comprise an opening means along which affords access to the stack and enables it to be torn open, or partly open, when the consumer wishes to extract the first of the compressed articles. Numerous opening means are known, a particularly suitable opening means has been described in European Patent application 425 008.

Plastic Covering

The primary function of the plastic covering is to protect the compressed flexible articles from the external environment, and, preferably, to provide a handle for carrying the whole package. The plastic covering preferably comprises an opening means which facilitates the removal of the compressed flexible articles, normally one at a time.

The plastic covering may be made out of any polymeric material, preferably a thermoplastic film, such as low density polyethylene (LDPE), high density polyethylene (HDPE), polyester, polypropylene, or combinations, or laminates of these.

The plastic may be made from virgin or recycled material, or a mixture of these.

In order to achieve the film of plastic invention a thin film of plastic is preferred for the covering; a film of low density polyethylene having a thickness less than 60 micrometers, and preferably less than 40 micrometers is most preferred. A film thickness of 30 micrometers has been found to be particularly suitable. Such thin films can be used because the thermoplastic film does not need to have a tensile strength sufficient to resist the forces exerted by the compressed, flexible articles. Hence, thermoplastic films may be used which have the same thickness as those used for packing a given number of flexible articles in their uncompressed state.

One embodiment of the invention provides a carrying handle as an integral part of the plastic covering. The construction of such a carrying handle may be any that is conventionally used in the art and does not form a part of the invention. One widely used construction comprises a carrying handle which is integral with the top panel of the covering. For example, the carrying handle may be formed from, and be unitary with, the top panel.

Another feature of a preferred embodiment of the invention is an opening means in the plastic covering. Any opening means that is conventionally used in the art may be found to be suitable. Such an opening means may take the form of a substantially continuous line of weakness, for example a line of perforations, and it may include an opening tab which enables the consumer to grip the plastic of the covering at a point adjacent to the opening means in order to tear the covering open. In particular, the opening means disclosed in EPA 349 050 may be advantageously used.

A convenient form for the plastic wrapping is that of the top-gusset or side-gusset type. The top-gusset type is illustrated in FIG. 1.

Although it is foreseen that the unit package comprising the paper wrapping will be contained within the plastic covering, the possibility of constructing the composite package such that the plastic covering is contained within the paper wrapping is not excluded. In a preferred embodiment of the invention, it is possible to optimise the environmental profile of the package by use of recycled materials for the wrapping and the covering, and to make recycling of the packaging materials as easy and economical as possible. In this embodiment, the outer covering is made from a transparent, unprinted film, and the paper wrapping bears printing and decoration. This arrangement enables the consumer to see the manufacturer's instructions through the transparent film, and also enables the manufacturer to identify the product and brand to the consumer. This embodiment is preferable from a recycling point of view because paper products can be more easily de-inked and subsequently recycled than plastic films.

Composite Package

The composite package 10 shown in FIG. 1 will now be described in more detail. This Figure shows a covering 19 made from a film of low density polyethylene having a film thickness of 30 micrometers which forms the outer layer of the package. The covering comprises a front panel 13 and a back panel 15 connected to one another by means of a pair of opposed end panels 14, 14'. The covering has a top panel 18 which is unitary with a carrying handle 16. The covering also comprises a line of weakness (perforations) 17 in the end panel 14 forming an opening means. The opening means is located such that it defines a predetermined portion of the end panel 14 of the covering 19, and enables the predetermined portion to be separated from the rest of the end panel in order to gain access to the contents. Contained within the covering there is a unit package 20 of compressed diapers 11 which are retained within a paper wrapping 12, the paper of which has a basis weight of 70 grams per square meter.

Figure 2:
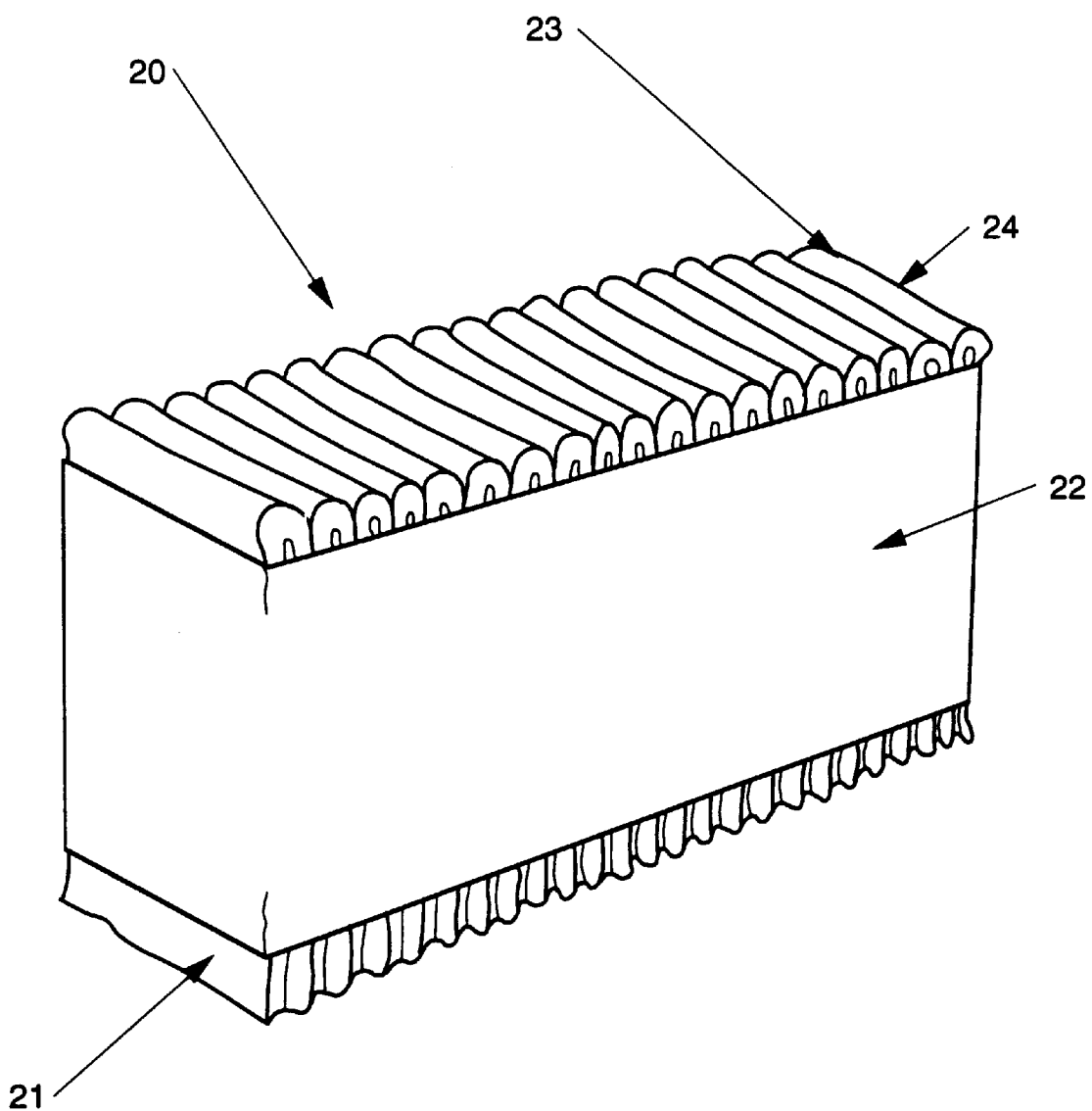
FIG. 2 shows a unit package of compressed flexible articles. The flexible articles illustrated have been folded and packed in a "head-to-head" configuration, i.e. with all of the folded edges on the same side of the unit package.
Figure 3:
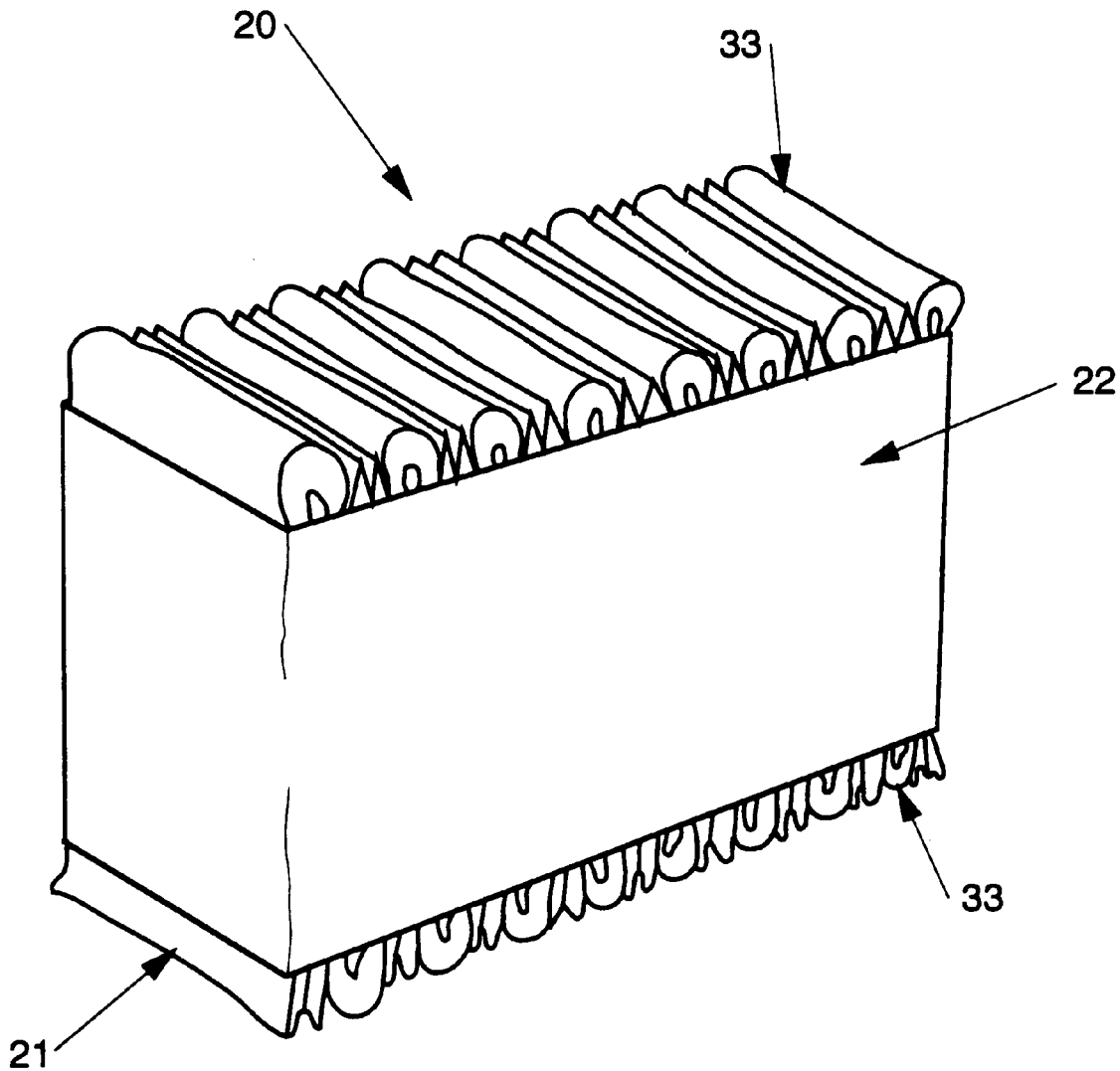
FIG. 3 shows an alternative type of unit package of compressed flexible articles. The flexible articles illustrated have been folded and packed in a "head-to-tail" configuration, i.e. with the folded edges alternately at opposite sides of the unit package.
Figure 4:
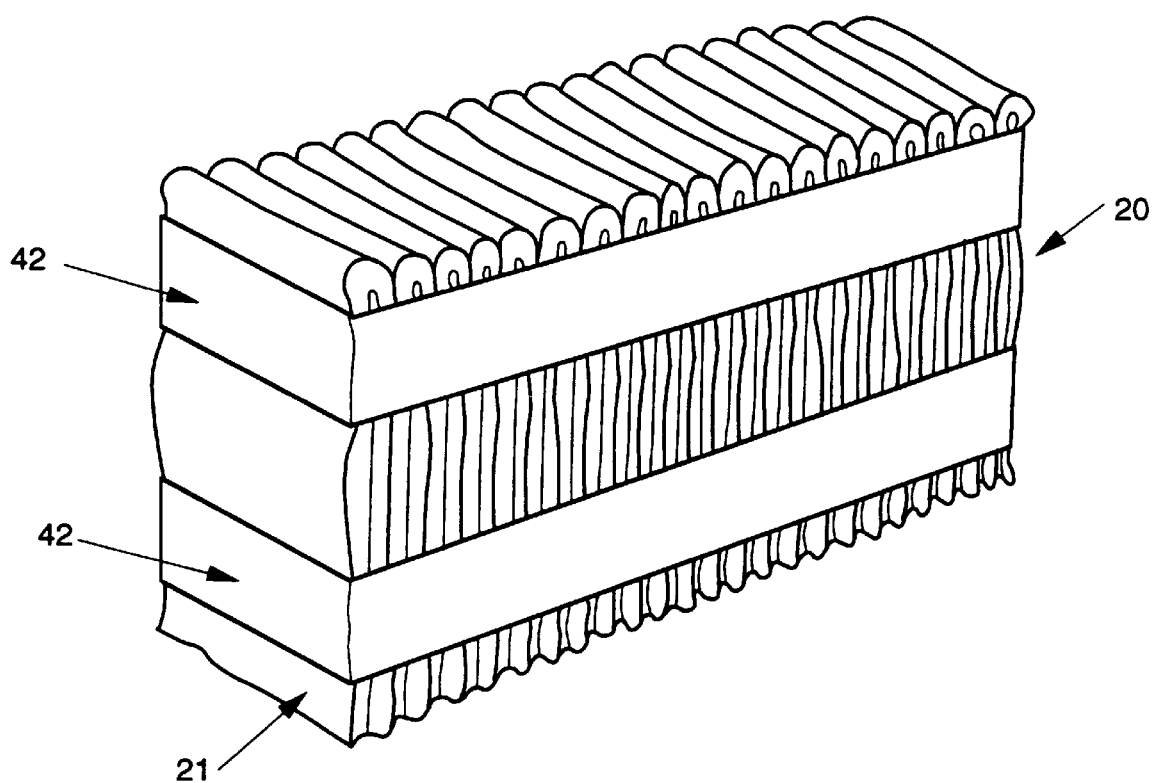
FIG. 4 shows another alternative type of unit package of compressed flexible articles in which the compressed unit package is retained within a pair of wrapping sleeves.

Alternative configurations of a suitable unit package can be more clearly seen in FIGS. 2, 3 and 4. FIG. 2 shows a unit package 20 which contains folded absorbent articles 21 which are maintained in the compressed state by a four-sided sleeve 22. The folded edges 23 of each of the absorbent articles lie on the same side of the package in a "head-to-head" configuration. In FIG. 3, the folded edges 33 of the absorbent articles lie alternately on opposite sides of the unit package in a "head-to-tail" configuration.

FIG. 4 shows another type of alternative unit package 20 in which a pair of sleeves 42 are used to maintain the flexible articles 21 in the compressed state.

Two alternative types of four-sided sleeve are shown in FIG. 5. In FIG. 5a, two strips of paper material have been folded and bonded together at two areas of overlap 54, 55. In FIG. 5b, a single strip of paper material has been folded back onto itself and bonded at an area of overlap 56.

In normal use, it is expected that the consumer will open the plastic outer covering 19 by using the perforated opening means 17 provided. The inner paper wrapper 12 will then also be broken open, or partly open, along an opening means to allow the removal of the diapers 11. The overall volume of the package may begin to increase once the paper wrapper has been broken in this way, and the diapers are able to begin to expand.

Packaging processes

According to another aspect of the invention, there is provided a method for assembling the package.

In general, the composite package may be assembled by carrying out the following operations:

a) compressing one or more stacks of flexible articles 11;
   b) forming one or more wrappings 12;
   c) forming a covering 19; and
   d) combining the compressed stacks, wrappings and covering obtained from these operations in any appropriate manner or order to form a finished composite package.

In a preferred embodiment of this aspect of the invention steps a) and b) are carried out as follows. A stack of flexible articles is compressed between two opposing plates or belts of a compression apparatus, a preformed wrapping sleeve is made according to the method described previously, said wrapping sleeve being positioned adjacent to or around the compression apparatus, and the compressed stack is transferred from the compression apparatus directly into the preformed wrapping sleeve.

In another alternative embodiment of the invention the paper wrapping may be preformed and fixed inside the outer plastic covering. In this embodiment the compressed stack is transferred directly from the compression apparatus into the preassembled paper wrapping and plastic covering. This embodiment results in only a single packing operation to pack the stack of compressed articles into the composite package.

However, in both of the previously described embodiments part of the initial compression of the articles is lost in the insertion process due to the clearance required within the perimeter of the wrapping during the insertion process.

A more preferred packing process employs the method described in U.S. Pat. No. 3,327,449 to carry out steps a) and b), the teaching of which is incorporated herein in its entirety by reference. According to this method, an apparatus (shown in FIG. 1 of U.S. Pat. No. 3,327,449) includes a slanted bed or table for supporting and positioning a stack of flexible articles between a stationary compression member and a moveable compression member. A paper supply means is used to supply a paper sheet over the members when they are moved together. Above the paper is a pair of receiving members which hold the compressed flexible articles and paper when moved upwardly by the compression members. In this position, edges of the paper are adhered together to complete the package. When the next package is partially wrapped and moved upwardly, it automatically pushes a completed package from the receiving members. The apparatus used is described in more detail between column 2, line 53, and column 5, line 47 of U.S. Pat. No. 3,327,449.

This technique results in the flexible articles retaining all of the compression applied by the compression apparatus, which means that either a smaller (more compressed) package is achieved, or, alternatively less initial compression of the flexible articles is needed to achieve a given amount of compression in the finished package.

Irrespective of the method used to compress and wrap the flexible articles, it is also necessary to form a suitable covering (step c). One way of doing this is by partially erecting a flexible bag made from a polymeric film comprising a front panel 13 and a back panel 15 connected to one another by means of a pair of opposed end panels 14, 14' said partially erected flexible bag having a top panel 18 secured about its periphery to said front, back and end panels, said flexible bag comprising at least one substantially continuous line of weakness 17 defining a predetermined portion of said end panel to be separated from remainder of said end panel, said partially erected flexible bag further having an open bottom end.

The composite package may then be completed by the steps of inserting one or more unit packages into the partially erected bag through the open bottom end, and securing said bottom panel in a closed position to complete said flexible bag.

Alternatively, in the embodiment described above in which the preformed paper wrapping is fixed inside the plastic covering, this may be done by preforming a paper wrapper in the manner previously described, partially erecting a flexible bag and placing the wrapper inside the bag by inserting it through the open bottom end. A stack of compressed articles may then be inserted into the paper wrapper and the bag closed by sealing the bottom end.

What is claimed is:

1. A package for compressed diapers comprising:

a) at least one unit package containing a plurality of compressed diapers;

b) an inner paper wrapping encircling said at least one unit package to maintain said plurality of compressed diapers in a compressed condition, said inner wrapping having at least four sides wherein at least two of said four sides are disposed parallel to a direction of compression of said compressed diapers; and c) an outer covering surrounding said at least one unit package external to said inner paper wrapping, said outer covering being made of a film of thermoplastic material having a strength insufficient to prevent said plurality of compressed diapers from expanding, said package thereby decoupling resistance of compression stresses from resistance of environmental stresses in order to provide a lightweight, inexpensive package.

2. The package of claim 1 wherein said inner paper wrapper is a printed sleeve and said outer covering is transparent so that recycling of said package is improved because said inner paper wrapper provides easier de-inking prior to recycling than does a printed plastic film.

3. The package of claim 1 wherein said inner paper wrapping has a tensile strength of at least 4 kN/m and an extensibility at rupture of less than 1.04.

4. The package of claim 1 wherein said film of thermoplastic material is low density polyethylene having a thickness of less than 60 micrometers.

* * * * *